United States Patent [19]
Karna et al.

[11] 4,069,018
[45] Jan. 17, 1978

[54] EXPLOSIVE GAS MONITORING METHOD AND APPARATUS

[75] Inventors: John D. Karna, Renton; Gregory K. Brock, Kelso; Daniel M. Shellhammer, Longview, all of Wash.

[73] Assignee: Weyerhaeuser Company, Tacoma, Wash.

[21] Appl. No.: 727,360

[22] Filed: Sept. 28, 1976

[51] Int. Cl.$^2$ ..................... G08B 21/00; G01N 33/00
[52] U.S. Cl. ................................ 23/232 E; 23/254 E; 340/237 R
[58] Field of Search ............. 23/232 E, 254 E, 255 E; 73/23, 25, 26, 27; 340/237 R, 228.1

[56] References Cited
U.S. PATENT DOCUMENTS

| | | | |
|---|---|---|---|
| 3,209,343 | 9/1965 | Dunham et al. | 23/255 E X |
| 3,236,603 | 2/1966 | Durrett et al. | 23/254 R |
| 3,478,579 | 11/1969 | Whitmore et al. | 73/27 R X |
| 3,549,327 | 12/1970 | Fergusson | 23/255 E X |
| 3,692,492 | 9/1972 | Poli, Jr. et al. | 23/232 E X |
| 3,765,842 | 10/1973 | Purt | 340/237 R X |
| 3,801,972 | 4/1974 | Kim et al. | 340/237 R |
| 3,973,848 | 8/1976 | Jowett et al. | 73/23 X |

*Primary Examiner*—Robert M. Reese
*Attorney, Agent, or Firm*—Christensen, O'Connor, Garrison & Havelka

[57] ABSTRACT

Monitoring of the recirculated atmosphere of an oxygen pulping reactor to determine when the inflammability level of combustible gases in the reactor atmosphere has reached a predetermined percentage of the lower explosive limit (LEL) of the reactor atmosphere in terms of combustible organic vapors and carbon monoxide is disclosed. Continuous or discrete samples of the reactor atmosphere are taken at spaced regions, and the samples are applied to: (1) flame ionization detectors, which determine the concentration of combustible organic vapors (e.g., aliphatic, olefinic, aromatic, acetylenic, alcohols, aldehydes, ketones, etc.) in the samples; and, (2) carbon monoxide analyzers, which determine the concentration of carbon monoxide in the samples. The outputs of the flame ionization detectors are calibrated in terms of percent LEL for the contributing combustible organic vapors and, thus, provide percent combustible organic vapor LEL information. The outputs of the carbon monoxide analyzers are calibrated in terms of percent LEL based on the carbon monoxide in the samples. The outputs of the flame ionization detectors are compared and the highest percent output is applied to an alarm and recording subsystem. These outputs are also compared to determine if they are close to one another. If the comparison indicates that a substantial difference exists, a differential sensor activates a further alarm to denote a wide variance that may indicate a faulty detector channel. Similarly, the outputs of the two carbon monoxide analyzers are compared and the highest percent output is applied to an alarm and recording subsystem. Also, if the outputs are substantially different a differential indicator is activated. In addition, in an alternate embodiment, the highest flame ionization output is summed with the highest carbon monoxide analyzer output and the result applied to a controller that continuously controls the position of a vent valve, as well as to an alarm and recording subsystem. Finally, an oxygen analyzer is provided for measuring the oxygen concentration of at least one of the reactor atmosphere samples.

32 Claims, 6 Drawing Figures

EXPLOSIVE GAS MONITORING METHOD AND APPARATUS

BACKGROUND OF THE INVENTION

This invention is directed to methods of and apparatus for monitoring gaseous atmospheres and, more particularly, to methods of and apparatus for monitoring the concentration of combustible gases in an atmosphere.

In recent years, major progress has been made toward the development of pulping apparatus for delignifying wood by the application of gaseous oxygen in an aqueous media. Of the proposed oxygen pulping systems, two-stage soda-oxygen pulping has received the most attention. In two-stage soda-oxygen pulping a first stage soda or alkaline delignification is followed by a second stage alkaline oxygen delignification. Preferably, the second stage delignification is performed in a recirculating atmosphere oxygen reactor. While a recirculating atmosphere oxygen reactor is preferred for cost reasons, the recirculation of the reactor atmosphere creates a potentially hazardous situation due to the gaseous and vaporous combustible products formed during the delignification process. More specifically, since the reactor atmosphere is recirculated, the concentration of combustible pulp degradation products, as well as volatile pulp and dilution zone constituents, in the gas phase, increases with time. The increase is such that after a period of time a combustible (explosive) level may be reached, unless the reactor atmosphere is vented, or the combustibles are removed in some manner. This time frame, which relates to the rate at which the foregoing items are produced, has been found to extend from a few hours to a few days, depending upon reactor design and conditions.

As those skilled in the art and others will readily recognize, there are two well-defined limits within which self-propagation of a flame (e.g. a deflagrative explosion) will take place upon ignition. These limits are defined as the upper explosive limit (UEL) and the lower explosive limit (LEL). The LEL is defined as the lowest concentration (% vol. basis) of a combustible gas that, when ignited with an open flame or spark, will propagate a flame. As the concentration of gases increases, a point is reached whereat the gas will burn at the point of ignition, but will not propagate a flame. This concentration is defined as the UEL. (These limits are sometimes also referred to as the upper and lower limits of inflammability).

It will be appreciated that, in order to prevent a potentially inflammable atmosphere from reaching its LEL, the concentration of combustible materials in the gas must be kept well below the LEL by, for example, effective venting to the earth's atmosphere. The present invention is directed to providing a method of and apparatus for monitoring a potentially inflammable atmosphere, particularly the atmosphere of an oxygen reactor used in an oxygen pulping system, to provide information about the concentration of combustibles in the reactor atmosphere. The information may take the form of a record, alarms, or a combination thereof, and may be used in combination with a control system to automatically control apparatus, such as a vent valve, adapted to reduce the concentration of combustible gases in the potentially inflammable atmosphere.

Therefore, it is a general object of this invention to provide a new and improved apparatus for monitoring the presence of combustible gases in a gaseous atmosphere.

It is a further object of this invention to provide a method of and apparatus for monitoring the presence of combustible gases in the atmosphere of an oxygen pulping reactor so as to provide information about the concentration of combustible gases in the reactor atmosphere such that action can be taken to reduce the concentration when it reaches a predetermined level.

In the past, catalytic combustibles analyzers have frequently been used to measure the concentration of combustibles in a gaseous atmosphere. While such devices are useful in certain environments, they possess serious disadvantages, which make them unsuitable for use in other environments. One particular disadvantage becomes significant when the atmosphere includes a variety of combustible components, such as exists in the atmosphere of an oxygen pulping reactor. Specifically, while catalytic combustibles analyzers are relatively accurate and precise when a single combustible component is contained in the atmosphere being analyzed, they become relatively imprecise when the atmosphere includes a variety of combustible components, because they respond to different components with different sensitivies and do not provide an output related to the concentration or percent LEL of the overall atmosphere. This result is particularly true when the atmosphere includes a variety of organic combustible vapors and carbon monoxide. A further disadvantage of catalytic combustibles analyzers is the rapid poisoning of the catalyst that occurs in the presence of a sulphur-containing gas.

Therefore, it is a further object of this invention to provide a more precise method of and apparatus for monitoring an atmosphere to provide information related to the concentration of combustible gases in the atmosphere.

It is a still further object of this invention to provide a new and improved method of and apparatus for determining when the concentration of combustible gases in an atmosphere has reached a predetermined percent of the lower explosive limit of the atmosphere.

It is a still further object of this invention to provide a new and improved method of and apparatus for monitoring the atmosphere of an oxygen pulping reactor to provide an indication related to the concentration of combustible gases in the atmosphere in terms of percent LEL.

SUMMARY OF THE INVENTION

In accordance with this invention, a method of monitoring a potentially inflammable atmosphere to determine when the concentration of combustible gases in the atmosphere has reached a predetermined percentage of the lower explosive limit of the atmosphere caused by selected constituents is provided. The method comprises the steps of: continuously or discretely sampling the atmosphere at at least two different points; determining the combustible organic vapors content of the samples in terms of percent LEL based on the combustible organic vapors present in the samples; determining whether or not the combustible organic vapors content of any of the samples is above a predetermined percent LEL; providing an indication when the combustible organic vapors content of any of the samples is above said predetermined percent LEL; determining the carbon monoxide content of the samples in terms of percent LEL based on the carbon monoxide present in the samples; determining whether or not the carbon monoxide content of any of the samples is above a predetermined percent LEL; and, providing an indication when the carbon monoxide content of any of the samples is above said predetermined percent LEL.

As an alternative to providing separate indications when the combustible organic vapors and the carbon monoxide contents are above predetermined percent LEL levels, the determined LEL levels are first combined and an indication is provided when the combined LEL level is above a predetermined percent LEL.

Also in accordance with this invention, an apparatus for monitoring a potentially inflammable atmosphere to determine when the concentration of combustible gases in the atmosphere has reached a predetermined percent of the lower explosive limit of the atmosphere caused by selected constituents is provided. The apparatus comprises two channels, a first channel for determining the concentration of combustible organic vapors in the atmosphere and, a second channel for determining the concentration of carbon monoxide (CO). Preferably, each channel includes two subchannels so that separate independent determinations can be made using samples taken from different regions of the atmosphere. The first or combustible organic vapors analyzer subchannels each include a flame ionization detector (FID) suitable for detecting the presence of combustible organic vapors and providing an output indicative of the concentration of combustible organic vapors (e.g. aliphatic, olefinic, aromatic, acetylenic, alcohol, aldehyde, ketone, etc. organic atoms) in the atmosphere in terms of percent LEL. Similarly, the second or carbon monoxide subchannels each include a carbon monoxide analyzer for detecting the presence of carbon monoxide in the atmosphere and providing an output indicative of the concentration of carbon monoxide in the atmosphere in terms of LEL.

In accordance with further features of this invention, the outputs of the flame ionization detectors are compared and the one denoting the highest concentration of combustible organic vapors, i.e., highest percent LEL, is applied to recording and indicating subsystems. Preferably, the indicating system includes one or more alarms that are energized when the concentration of combustible organic vapors reaches predetermined percent LEL levels, such as 15 and 30 percent LEL. Similarly, the outputs of the CO analyzers are compared and the analyzer output denoting the highest level of carbon monoxide, i.e., highest percent LEL, is applied to recording and indicating subsystems. Again, preferably, the indicating subsystem includes alarms that are energized when the carbon monoxide level reaches predetermined percent LEL level, such as 15 and 30 percent LEL.

As an alternative (or an addition) to providing separate recording and indicating subsystems for the first and second channels, the determined combustible organic vapors channel LEL information and the carbon monoxide channel LEL information are combined and the resulting combination applied to recording and indicating subsystems. Again, preferably, such an indicating subsystem includes alarms that are energized when the combined level reaches a predetermined percent LEL level, such as 40 and 60 percent LEL.

In accordance with still further features of this invention, an optional oxygen analyzer measures the oxygen content of the atmosphere. The output of the oxygen analyzer is connected to the input of a continuous recorder that records the level of oxygen in the atmosphere.

In accordance with yet other features of this invention, the samples are applied to sample conditioners, which suitably condition the samples prior to applying them to the flame ionization detectors and the carbon monoxide analyzers. In addition, preferably, located between the sample conditioners and the carbon monoxide analyzers are carbon monoxide conditioners and regulators that further condition and regulate the portions of the samples applied to the carbon monoxide analyzers.

It will be appreciated from the foregoing summary that the invention comprises a new and improved system for monitoring a potentially inflammable atmosphere. Inflammability is denoted in percent LEL both in terms of combustible organic vapors and carbon monoxide. Thus, both the organic and inorganic components contributing to the inflammability of an atmosphere, such as an oxygen pulping reactor atmosphere, are monitored. In addition to controlling recorders and alarms, the generated information can be used for automatic control purposes, such as the control of automatic vent valves and/or reactor shut down. Reliability is enhanced as a result of the use of two subchannels in each monitoring channel.

BRIEF DESCRIPTION OF THE DRAWINGS

The foregoing objects and many of the attendant advantages of this invention will become more readily appreciated as the same becomes better understood by reference to the following detailed description and taken in conjunction with the accompanying drawings wherein:

FIG. 1A is a partially block and partially schematic diagram of a modification or addition to the embodiment illustrated in FIG. 1;

DESCRIPTION OF THE PREFERRED EMBODIMENT

Figure 1:
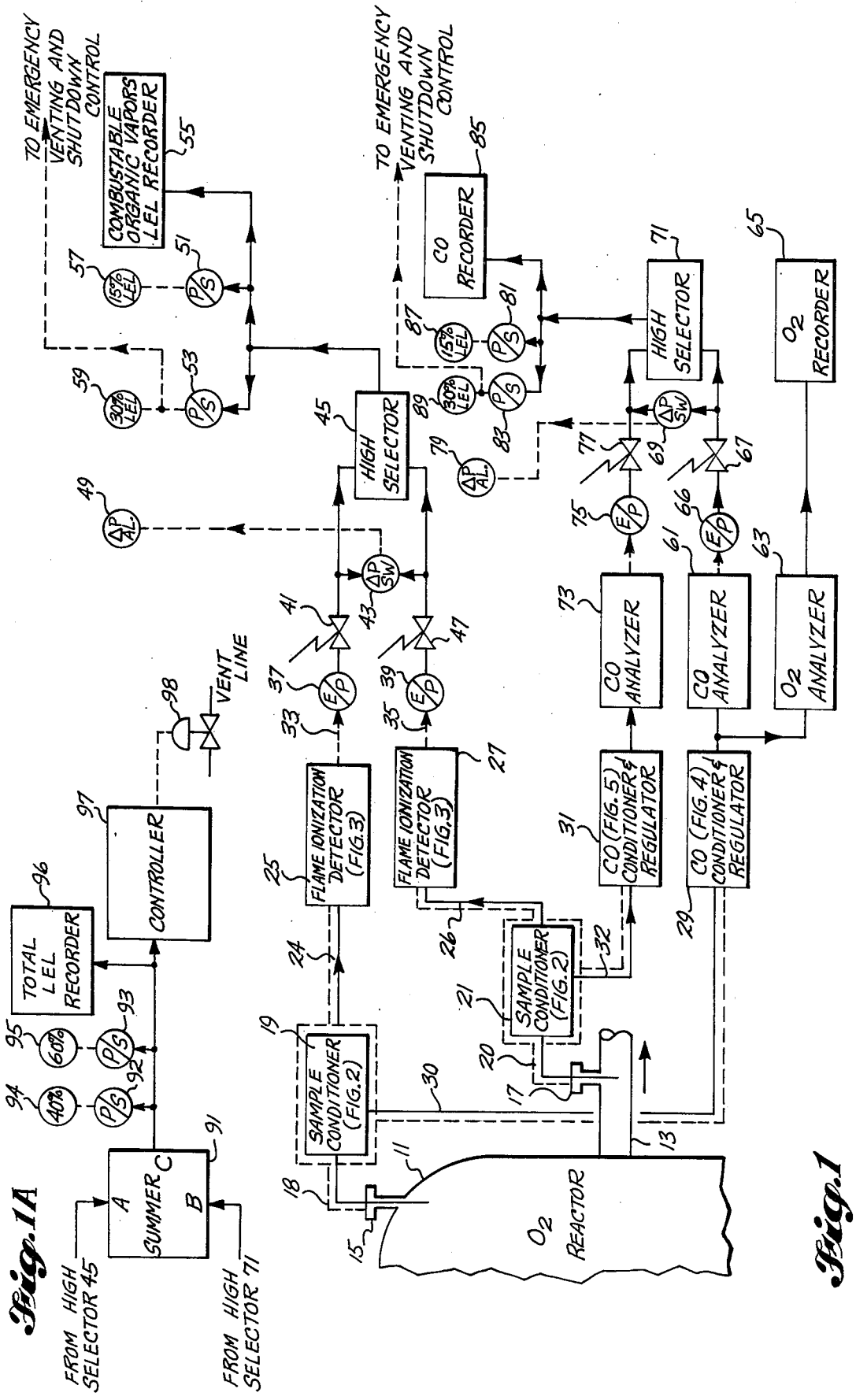
FIG. 1 is a partially block and partially schematic diagram of a preferred embodiment of an apparatus formed in accordance with the invention.

Prior to describing the preferred embodiment of the invention, a brief discussion of the LEL of organic compounds and the utilization of a flame ionization detector (FID) to measure the LEL of a mixture of combustible organic compounds is set forth. It is believed this discussion will assist in providing a better understanding of the invention and its advantages.

As will be readily appreciated by those skilled in the art to which the present invention relates, the lower explosive limit (LEL) of a mixture of both organic and inorganic combustables can be determined utilizing LeChatelier's principle. That is, the mixture LEL can be determined using the following equation:

$$LEL = \frac{100}{\Sigma P_i/N_i}$$

Where:
$P_i$ = explosive gas concentration on an air free basis
$N_i$ = LEL for each gas It will also be readily appreciated by those skilled in the art to which this invention relates that combustible or organic compounds have LEL's that vary over a relative wide range. The invention recognizes that if these LEL's are combined with the number of carbon atoms and the fractional response of an FID for a particular compound a usable number that is relatively constant is developed. In this regard, attention is directed to the following table:

| COMPOUND | LEL | NO. OF CARBON ATOMS | FRACTIONAL FID RESPONSE | (LEL × N) |
|---|---|---|---|---|
| METHANE | 5.0 | 1 | 1.0 | 5.0 |
| ETHYLENE | 2.75 | 2 | .95 | 5.23 |
| METHANOL | 6.72 | 1 | .9 | 6.03 |
| ACETONE | 2.55 | 3 | .66 | 5.05 |
| ACETALDEHYDE | 3.97 | 2 | .6 | 4.76 |
| ETHANOL | 3.28 | 2 | .95 | 6.23 |
| TURPENTINE | 0.8 | 10 | .99 | 7.92 |
| NONANE | 0.83 | 9 | 1.0 | 7.47 |
| METHYL CYCLOHEXANE | 1.15 | 7 | 1.0 | 8.05 |
| GLYCEROL ALDEHYDE | 2.5 | 3 | .66 | 4.95 |

Where:
N = number of detected carbon atoms in one molecule of the compound = number of carbon atoms times fractional response of the FID The average of last column of the foregoing table is 6.07 and the individual factors making up this average vary by only about ±30%. Therefore, for practical purposes, the LEL × N product can be considered a constant, with a value of 6.

It is known that the instrument response of a flame ionization detector to a compound X is proportional to the molar concentration of the combustible vapor of X and the number of carbon atoms in one molecule of compound X. Or, in the form of an equation:

$$M_x \alpha\, C_x N_x$$

Where:
$C_x$ is equal to the molar concentration of the combustible vapor of compound X
$M_x$ is equal to the instrument response for compound X
$N_x$ equal the number of detected carbon atoms in one molecule of compound X Since as shown above, LEL times N equals a constant, the foregoing equation can be rewritten as:

$$M_x \alpha\, \frac{C_x}{(LEL)_x}$$

Or for a mixture:

$$M = \sum_{x=1}^{n} M_x \alpha \sum_{x=1}^{n} \frac{C_x}{(LEL)_x}$$

Where:
$n$ relates to the different combustible components in the mixture.

It will be recognized that for a normalized instrument output (M=1), the above equation is merely a restatement of LeChatelier's principle. Thus, the flame ionization detector has been shown to respond to each combustible organic compound (vapor) in proportion to the contribution it makes to the mixture LEL. Consequently, the output, in essence, is in terms of the percent LEL of the mixture based on the combustible organic components in the mixture. While this conclusion is only approximately true because of the assumption that the LEL × N is a constant, it is sufficiently accurate to make a flame ionization detector a satisfactory indicator of the percent LEL of a mixture.

In accordance with the invention, flame ionization detectors are utilized to provide information in terms of percent LEL based on the combustible organic vapors in the mixture being monitored. Combustible organic vapors include molecules of the type listed in the foregoing table. However, since components other than combustible organic vapors, namely carbon monoxide, also contribute to the inflammability of a mixture and are present in an oxygen pulping reactor atmosphere, and since the LEL effect of such components cannot be measured by a flame ionization detector, the flame ionization detector output alone does not provide complete information about the inflammability of the monitored atmosphere. In order to provide this additional information the invention includes CO analyzers. Further, an indication of the total percent LEL is obtained by summing the percent LEL's derived by the flame ionization detector and the carbon monoxide analyzer in full accord with LeChatelier's principle. Moreover, rather than the inflammability of the reactor atmosphere being analyzed in only one region, the atmosphere's inflammability is analyzed at different, spaced regions.

Figure 2:
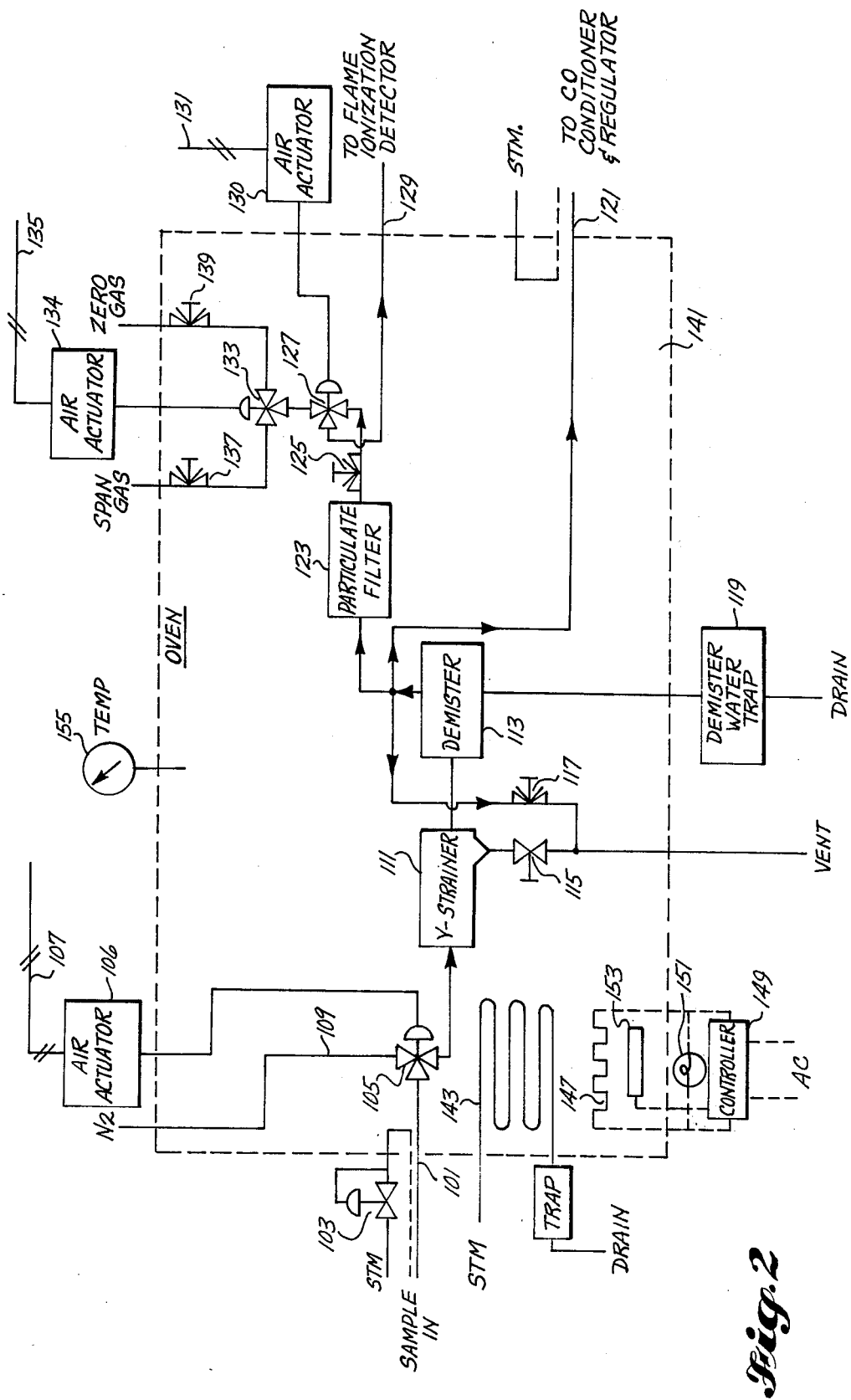
FIG. 2 is a partially block and partially schematic diagram of a sample conditioner suitable for use in the embodiment of the invention illustrated in FIG. 1.

Turning now to a description of the preferred embodiments of the apparatus of the invention; illustrated in FIG. 1 is an $O_2$ reactor 11 suitable for use in a two-stage soda-oxygen pulping system, wherein the atmosphere of the reactor is recirculated. The recirculated atmosphere leaves the $O_2$ reactor via an output pipe 13 and returns via an input pipe (not shown). Located in the upper region of the reactor 11 is a first sample port 15; and, located in the output pipe 13 is a second sample port 17. The first sample port 15 is connected to a first sample conditioner 19 via a first steam heated pipe 18 and the second sample port 17 is connected to a second sample conditioner 21 via a second steam heated pipe 20. (As used in the drawings: a dashed line adjacent to a solid line denotes a steam heated pipe; a solid line alone denotes a simple pipe; and, a dashed line alone denotes an electrical connection. A dashed line around a box indicates that the item in the box is in a temperature controlled environment). A sample conditioner suitable for forming the first and second sample conditioners is illustrated in FIG. 2 and hereinafter described.

The sample conditioners 19 and 21 condition the $O_2$ reactor atmosphere samples, which are preferably continuously taken (but may be discretely taken) at the sample ports, such that they are suitable for application to flame ionization detectors (for combustible organic vapors LEL analysis) and to CO conditioners and regulators. The CO conditioners and regulators further condition the samples such that they become suitable for application to CO analyzers. Thus, the sample conditioners have combustible organic vapors and CO (carbon monoxide) outputs.

The combustible organic vapors output of the first sample conditioner 19 is connected to the input of a first flame ionization detector (FID) 25 via a third heated pipe 24. The combustible organic vapors output of the second sample conditioner 21 is connected to the input of a second flame ionization detector (FID) 27 via a fourth heated pipe 26. The CO output of the first sample conditioner 19 is connected to the input of a first CO conditioner and regulator 29 via a fifth heated pipe 30; and, the CO output of the second sample conditioner 21 is connected to the input of a second CO conditioner and regulator 31 via a sixth heated pipe 32.

As discussed above, the flame ionization detectors 25 and 27 each produce an output whose value is related to the percent LEL based on the level of combustible organic vapors in the atmosphere samples analyzed. These outputs take the form of electrical signals, which are applied via first and second wires 33 and 35, respectively, to the electrical inputs of first and second electrical-to-pressure (E/P) converters 37 and 39. The pressure output of the first E/P converter 37 is connected through a first electrically controlled valve 41 to one input of a combustible organic vapors differential pressure switch 43 and to one input of a combustible organic vapors high selector 45. The pressure output of the second E/P converter 39 is connected through a second electrically controlled valve 47 to the other side of the combustible organic vapors differential pressure switch 43 and the other side of the combustible organic vapors high selector 45. The first and second electrically controlled valves allow down stream indicating and recording devices (hereinafter described) to be disconnected from the FID's during calibration of the FID's.

The combustible organic vapors differential pressure switch detects the difference in pressure between the outputs of the first and second E/P converters and produces an electrical signal when the differential pressure therebetween surpasses a predetermined level. The electrical signal is applied to and activates an combustible organic vapors differential pressure alarm 49. Such activation may occur, for example, if one of the combustible organic vapors subchannels fails.

The combustibles organic vapors high selector 45 selects which of the outputs of the first and second E/P converters is higher in pressure (thereby denoting a higher percent LEL), and applies this output to first and second pressure switches 51 and 53. The output of the combustible organic vapors high selector is also applied to a continuous recorder 55, which is calibrated in percent LEL. The output of the first pressure switch 51 produces an electrical output when the output chosen by the high selector is at or above 15% LEL. The second pressure switch 53 produces an electrical output when the chosen output is at or above 30% LEL. Thus, these signals occur when the combustible organic vapors of the sample reach levels equal to 15% and 30%, respectively, of the concentration of combustible organic vapors that, when ignited with an open flame or spark will propagate a flame. The outputs of the first and second pressure switches 51 and 53 are applied to first and second combustible organic vapors LEL alarms 57 and 59, respectively. Thus, the first alarm 57 is energized when the combustible organic vapors reach 15% LEL and the second alarm is energized when the combustible organic vapors reach 30% LEL. The output of the pressure switch operating the second alarm may also be used to control an emergency venting and shutdown control, if desired, as illustrated in FIG. 2.

It will be appreciated from the foregoing description that, in essence, a combustible organic vapors analyzing channel including two separate flame ionization detector subchannels forms part of the invention. The flame ionization detector subchannels each separately analyze a sample of the $O_2$ reactor atmosphere for combustible organic vapors content and provide a normalized output in terms of percent LEL. The flame ionization detector outputs are analyzed to determine whether there is a substantial difference therebetween, and the highest output is chosen for application to alarm controlling LEL level sensors (e.g. pressure switches). The LEL level sensors are set such that audio or visual alarms are produced as the percent LEL increases. In addition, a continuous record is made of the percent LEL occuring on the highest percent LEL subchannel.

The output of the first CO conditioner and regulator 29 is applied to a first CO analyzer 61 and to an $O_2$ analyzer 63. The output of the $O_2$ analyzer 63 is applied to an $O_2$ recorder 65.

The first CO analzyer may, for example comprise a UNOR 6 CO analyzer produced by MAIHAK GmbH of West Germany. Such an analyzer determines the CO content of its input and provides an output that can be calibrated in terms of percent LEL based on the carbon monoxide content of the sample analyzed. The output of ther first CO analyzer 61 is applied via a third E/P converter 66 connected in series with a third electrically controlled valve 67 to one input of a CO differential pressure switch 69 and one input of a CO high selector 71.

The output of the second CO conditioner and regulator 31 is applied to the input of a second CO analyzer 73. The second CO analyzer may, for example, comprise a Beckman 864 CO analyzer produced by the Beckman Instruments Company of Fullerton, California. This type of CO analyzer also produces an electrical output that can be calibrated in terms of percent LEL based on the amount of carbon monoxide in a sample. The electrical output of the second CO analyzer 73 is connected to the electrical input of a fourth electrical-to-pressure (E/P) converter 75. The output of the fourth E/P converter 75 is connected via a fourth electrically controlled valve 77 to the other input of the CO differential pressure switch 69 and the other input of the CO high selector 71. (Again, the third and fourth electrically controlled valves disconnect downstream devices during calibration, in this case CO analyzer calibration.) The CO differential pressure switch 69 senses the pressure applied to its opposite sides and, when the differential pressure therebetween achieves a predetermined level produces an electrical signal, which is applied to a CO differential pressure alarm 79. Such a signal may occur, for example, due to failure of one of the CO analyzer subchannels.

As with the combustible organic vapors high selector 45, the CO high selector 71 applies its highest level input to its output. The output of the CO high selector 71 is connected to a pair of CO pressure switches 81 and 83 and to a CO recorder 85. The first CO pressure switch 81 produces an electrical output when the output chosen by the CO high selector is at or above 15% LEL based on the amount of CO in the related sample; and, the second CO pressures switch produces an electrical output at 30% LEL. The output of the first CO pressure switch 81 is applied to a first CO LEL indicator 87 and the output of the second CO pressure switch 83 is applied to a second CO LEL indicator 89. Thus, when the selected output is above 15% LEL the first indicator 87 is energized and when the output is above 30% LEL the second indicator 89 is energized. If desired, the output of the second pressure switch 83 may be connected to an emergency venting and shutdown control to provide automatic shutdown of the $O_2$ reactor when the CO LEL level rises above 30% LEL.

FIG. 1A illustrates a modification of (or addition to) the embodiment of the invention illustrated in FIG. 1 and comprises: a summer 91; first and second total pressure switches 92 and 93; first and second total alarms 94 and 95; a total LEL recorder 96; and, a continuous controller 97. The summer 91 is adapted to receive a pair of input signals at input ports designated A and B and produce an output at a port designated C. The output level is the sum (e.g. C = A + B, base on LEL percents) of the levels of the inputs and operates in accordance with LeChatelier's principle.

Input port A of the summer 91 is connected to the output of the combustible organic vapors high selector 45 and input port B is connected to the output of the CO high selector 71. Output port C of the summer 91 is connected to: the inputs of the first and second total pressure switches 92 and 93; the input of the total LEL recorder 96 and the input of the controller 97. The first and second total pressure switches are electrically connected to the first and second total alarms 94 and 95, respectively. Preferably, the first total pressure switch 92 produces an electrical output when the output of the summer is at or above 40% LEL; and, the second total pressure switch 93 produces an electrical output when the output fo the summer is at or above 60% LEL. Thus, the first and second total alarms are energized at 40% and 60% LEL, respectively.

The continuous controller 97 produces an electrical signal in accordance with the combined LEL output of the summer, which is applied to, and controls the position of, an electrically controllable vent valve 98. The vent valve is coupled to the $O_2$ reactor such that the atmosphere of the $O_2$ reactor is continuously vented in accordance with the electrical control signals produced by the controller 97. These control signals, in turn, are determined by the level of the output of the summer. The level of the summer, as discussed above, is in percent LEL. Thus, the reactor atmosphere is automatically vented in accordance with the measured percent LEL based on combustible organic vapors and CO content.

It will be appreciated from the foregoing description that the invention, in addition to the combustible organic vapors channel, also includes a carbon monoxide channel, which includes two subchannels. Further, connected to one of the subchannels is an $O_2$ analyzer.

In summary, the invention first conditions samples taken from two different regions of the atmosphere being monitored. The conditioned samples are analyzed by flame ionization detectors and CO analyzers to determine percent LEL based on combustible organic vapors content and carbon monoxide content, respectively. If the percentages (or the combined percentages) rise above preset levels, lower and then higher level alarms are energized. If the higher levels are reached an automatic shutdown sequence may be implemented. Further, highest (and/or combined) combustible organic vapors and CO LEL percentages are continuously recorded. And, a combined LEL controls a continuous venting subsystem. With respect to venting, it should be noted that the vent action controls or maintains the LEL summation at or below a predetermined level. Venting of the $O_2$ reactor atmosphere may be either to the earth's atmosphere directly, or to the earth's atmosphere via a suitable device or devices adapted to remove undesirable constituents from the reactor atmosphere prior to its release to the earth's atmosphere.

FIG. 2 is a partially block and partially schematic diagram of a sample conditioner suitable for use as either the first or second sample conditioners 19 and 21 forming a portion of the preferred embodiment of the invention illustrated in FIG. 1. The sample conditioner illustrated in FIG. 2 receives a continuous sample (or discrete samples) from the sample port 15 or 17 at a sample inlet port 101. The sample input pipe 18 or 20, as previously noted, is heated. Steam heat is provided via a pressure control steam valve 103. The temperature of the steam must be above the temperature of the reactor to prevent condensation of high molecular weight organic materials and water, 300° F, for example. The sample inlet port 101 is connected to the inlet of a first air-actuated three-way valve 105. The first air-actuated three-way valve 105 has its actuator element 106 connected to a suitable external air source via a control line 107. The first outlet of the first air-actuated three-way valve 105 is connected via a purge line 109 to a suitable source of purge gas, such as nitrogen ($N_2$). The second outlet of the first air-actuated three-way valve 105 is connected to the input of a Y-strainer 111. The gas outlet of the Y-strainer 111 is connected to the input of a demister 113. The drain outlet of the Y-strainer 111 is connected to a vent outlet via a mechanically controlled shut-off valve 115. The gas outlet of the demister 113 is also connected, via a first mechanically controlled regulator valve 117, to the vent outlet. The water outlet of the demister 113 is connected to a drain outlet via a demister water trap 119.

The gas outlet of the demister is also connected to a CO outlet port 121. The CO outlet port 121 is connected to the appropriate CO conditioner and regulator 29 or 31 via the related steam heated connecting pipe 30 or 32, as illustrated in FIG. 1.

The gas outlet of the demister 113 is also connected to the input of a particulate filter 123. The outlet of the particulate filter 123 is connected via a second mechanically actuated regulating valve 125 to one inlet of a second air-actuated three-way valve 127. The actuator element 130 of the second air-actuated three-way valve 127 is connected via a line 131 to a suitable air source. The outlet of the second air-actuated three-way valve 127 is connected to a flame ionization detector outlet port 129 that is connected to the appropriate flame ionization detector 25 or 27.

The second inlet of the second air-actuated three-way valve 127 is connected to the outlet of a third air-actuated three-way valve 133. The third air-actuated three-way valve 133 has its actuator element 134 connected to a suitable air source via a line 135. The first inlet of the third air-actuated three-way valve 133 is connected to a suitable span (calibrating) gas source via a third mechanically actuated regulator valve 137. The second inlet of the third air-actuated three-way valve 133 is connected to a zero gas (a gas free of the component being measured) source via a fourth mechanically actuated regulator valve 139.

All of the elements illustrated in FIG. 2 and previously described, except for the steam valve 103, the demister water trap 119, and the air actuators are mounted in an oven 141. The oven is both steam and electrically heated, with the electrical heat providing a redundant source in order to insure that the oven heat is maintained above the temperature of the $O_2$ reactor to prevent condensation of moisture and organic components. Steam heat is provided by a steam radiator apparatus that comprises a radiator element 143 formed of a coil of suitable tubing. One end of the coil is connected to a steam source and the other end is connected, via a trap 145, to a drain. Electrical heat is provided by an electrical heater that includes a heater element 147 connected to a controller 149. The controller is located externally of the oven 141. The controller is connected to a suitable source of power, such as an AC source. An indicator light 151 is connected across the output of the controller to indicate when the controller is applying power to the heater element 147. Further, a thermostat 153 is located inside of the oven and connected to the controller 149. In accordance with the sensed temperature information, the controller 149 applies power to the heater so as to maintain the temperature inside of the oven 141 at a predetermined level. The temperature inside of the oven may be displayed on an indicator 155 attached to a suitable temperature sensing element (not shown) mounted inside of the oven 141.

As will be appreciated by those skilled in the art from reviewing FIG. 2 and the foregoing discussion, the sample conditioners filter particulates and mist from the sample gas stream. Further, they provide for the application of zero and span calibration gases to the flame ionization detector for calibration purposes. In addition, they provide for the application of a purge gas (nitrogen) to clear the sample input line of accumulated debris. Preferably, the sample conditioners are located close to the sample ports of the oxygen reactor to provide pressure drops so that long lines extending to the flame ionization detectors don't create excessive response times.

Figure 3:
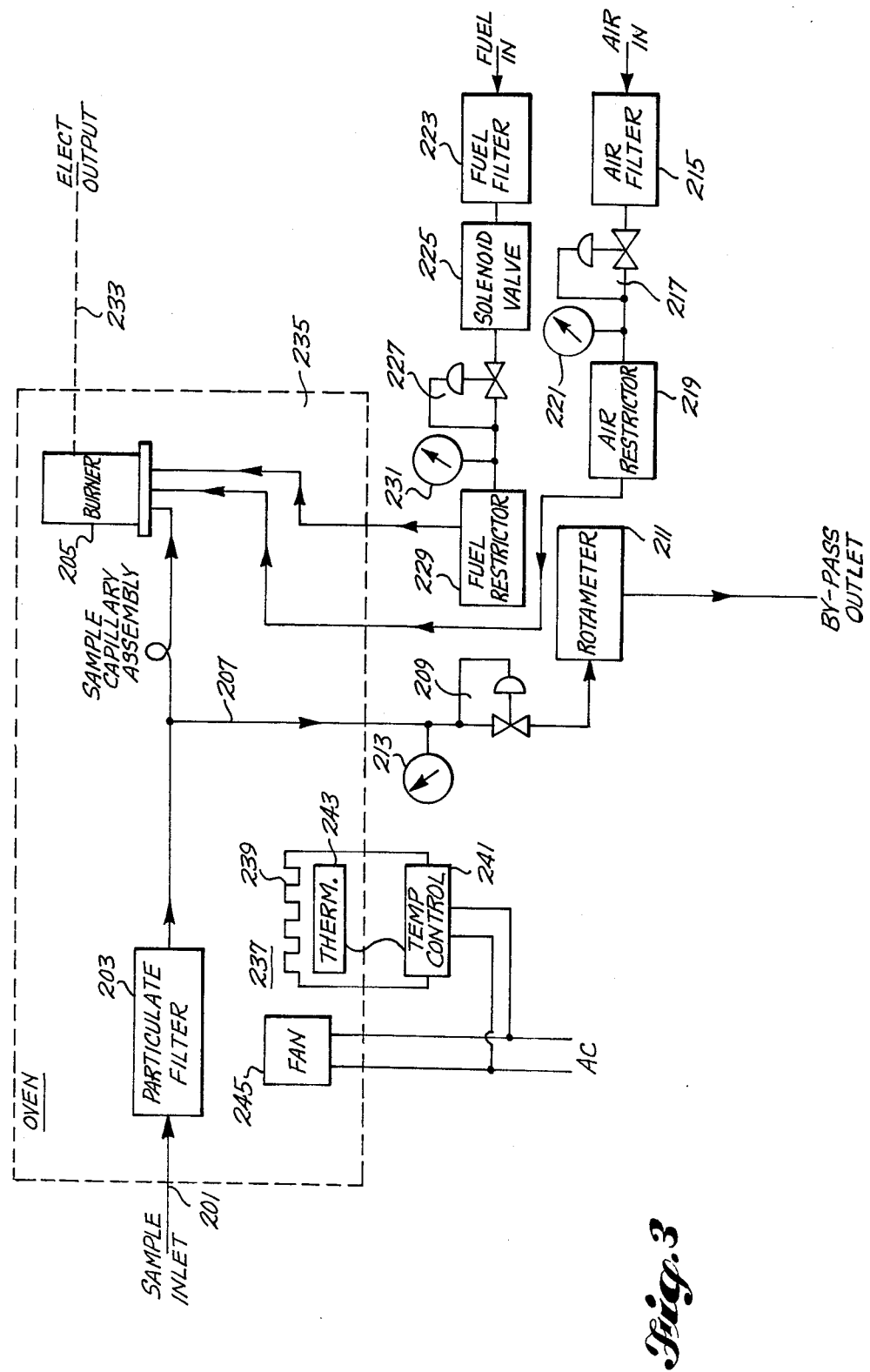
FIG. 3 is a partially block and partially schematic diagram of a flame ionization detector suitable for use in the embodiment of the invention illustrated in FIG. 1.

FIG. 3 illustrates a flame ionization detector suitable for use in the embodiment of the invention illustrated in FIG. 1. The flame ionization detector illustrated in FIG. 3 includes a sample inlet port 201 suitable for connection to the flame ionization detector outlet port 129 of the sample conditioner illustrated in FIG. 2. The sample inlet port 201 is connected to the input of a particulate filter 203. The output of the particulate filter 203 is connected, via a sample capillary assembly 204, to the sample input of a burner 205.

The output of the particulate filter 203 is also connected to a sample by-pass line 207. The sample by-pass line 207 extends to a by-pass outlet via a sample pressure regulator valve 209 and a by-pass rotameter 211, connected in series. The rotameter may be a 0–12 SCFH (standard cubic feet per hour) rotameter for example. A by-pass pressure indicating gauge 213 is connected to the by-pass line 207.

A suitable source of burner air is applied through an air filter 215 to an air pressure regulator valve 217. The output of the air pressure regulator valve 217 is connected through an air restrictor 219 to the air input of the burner 205. An air pressure gauge 221 is connected between the air pressure regulator valve 217 and the air restrictor 219 to provide an indication of the pressure of the air applied to the burner 205.

A suitable source of burner fuel is connected through a fuel filter 223 and a series connected solenoid valve 225 to a fuel pressure regulator valve 227. The output of the fuel pressure regulator valve 227 is connected through a fuel restrictor 229 to the fuel input of the burner 205. Fuel pressure is indicated on a fuel pressure gauge 231 connected between the fuel pressure regulator valve 227 and the fuel restrictor 229. In accordance with conventional flame ionization detector technology, the burner 205 burns the samples it receives and, in the process creates ions, which are collected. The collected ions, in turn, control output current whose magnitude is related to the value of the combustible organic vapors contained in the sample. The electrical output current is produced on an electrical conductor 233.

The particulate filter 203 and the burner 205 are located inside of an oven 235. The temperature in the oven is controlled by an electrical heater assembly 237. The electrical heater assembly 237 includes an electrical coil 239 connected to a temperature control 241 located outside of the oven 235. The temperature control is connected to a suitable source of power, such as an AC line power. Located inside of the oven 235 is a thermostat 243. The thermostat 243 is connected to temperature control 241. In addition, a fan 243 is mounted in the oven so as to blow air across the coil 237. In operation, the thermostat 243 measures the temperature in the oven and applies a related temperature signal to the temperature control. In accordance with this temperature signal, the temperature control controls the heat produced by the coil 239. The fan 245 blows across the coil and circulates the heat produced by the coil.

Figure 4:
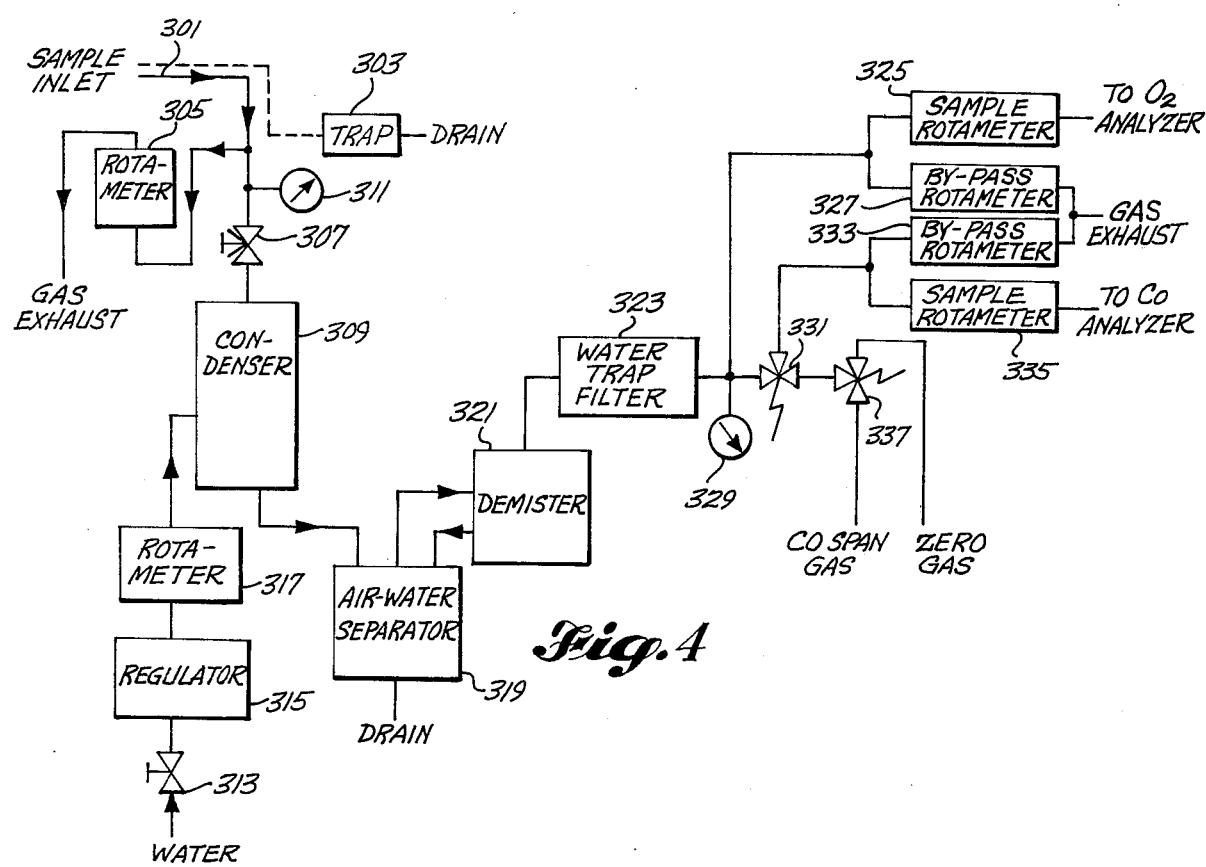
FIG. 4 is a partially block and partially schematic diagram of a CO conditioner and regulator suitable for use with the one of the carbon monoxide analyzers (and the $O_2$ analyzer) illustrated in FIG. 1; and, FIG. 5 is a partially block and partially schematic diagram of a sample conditioner and regulator suitable for use with the other carbon monoxide analyzer illustrated in FIG. 1.

FIG. 4 is a partially block and partially schematic diagram of a CO conditioner and regulator suitable for use in the embodiment of the invention illustrated in FIG. 1 for connecting the first sample conditioner 21 to the first CO analyzer 61, and to the $O_2$ analyzer 63. The CO conditioner and regulator illustrated in FIG. 4 is connected to the output of the first sample conditioner 21 at a sample inlet 301. The steam conduit of the heated pipe 30 extending between the illustrated CO conditioner and analyzer and the first sample conditioner is connected to a drain via a trap 303. The sample inlet 301 is connected through a gas rotameter 305 to a gas exhaust. The gas rotameter may be a 0–40 l/M (liters per minute) rotameter, for example. The sample inlet is also connected, via a mechanically actuated regulating valve 307, to the inlet of a condensor 309. Further, the sample inlet is connected to a pressure gauge 311. A water inlet is connected via a mechanically actuated on-off valve 313, in series with a regulator 315 and a water rotameter 317, to the water input of the condensor 309. The water rotameter may be a 0–40 GPH (gallons per hour) rotameter, for example.

The output of the condensor 309 is connected to the input of an air-water separator 319. The water outlet of the air water separator is connected to a drain. The gas outlet of the air-water separator 319 is connected to the inlet of a demister 321. The water outlet of the demister 321 is recirculated back to the air-water separator 319. The gas outlet of the demister 319 is connected through a water trap filter 323 to the inlets of an $O_2$ sample rotameter 325 and an $O_2$ bypass rotameter 327. The outlet of the $O_2$ sample rotameter is connected to the $O_2$ analyzer 63 (FIG. 1) and the outlet of the $O_2$ bypass rotameter 327 is connected to a gas exhaust. The $O_2$ sample rotameter may be a 0–180 SCC/M (standard cubic centimeters per minute) rotameter and the $O_2$ by-pass rotameter may be a 0–1.8 l/M rotameter, for examples.

The outlet of the water trap filter is also connected to a pressure gauge 329 and to one inlet of a first electrically controlled three-way valve 331. The outlet of the first electrically controlled three-way valve 331 is connected to the inlet of a CO bypass rotameter 333 and to the inlet of a CO sample rotameter 335. The outlet of the CO bypass rotameter 333 is connected to the gas exhaust. The outlet of the CO sample rotameter 335 is connected to the inlet of the CO anaylzer 61 (FIG. 1). The CO sample and by-pass rotameters may be the same as the $O_2$ sample and by-pass rotameter (i.e. have the same flow ranges).

The second inlet of the first electrically controlled three-way valve 331 is connected to the outlet of a second electrically controlled three-way valve 337. The first inlet of the second electrically controlled three-way valve 337 is connected to a source of CO span (calibration) gas and the second inlet is connected to a source of zero gas.

As will be appreciated by those skilled in the art and others the CO conditioner and regulator illustrated in FIG. 4 conditions and regulates the sample gas. The conditioning and regulating is such that the sample becomes suitable for CO and $O_2$ analysis by CO and $O_2$ analyzers, such as the UNOR 6 CO analyzer, referenced above and the Taylor OA-137 $O_2$ analyzer produced by Taylor Instruments Co. of Marshalltown, Iowa. In addition, provision is made to provide a CO span gas and zero gas for use in calibrating the CO analyzer.

Figure 5:
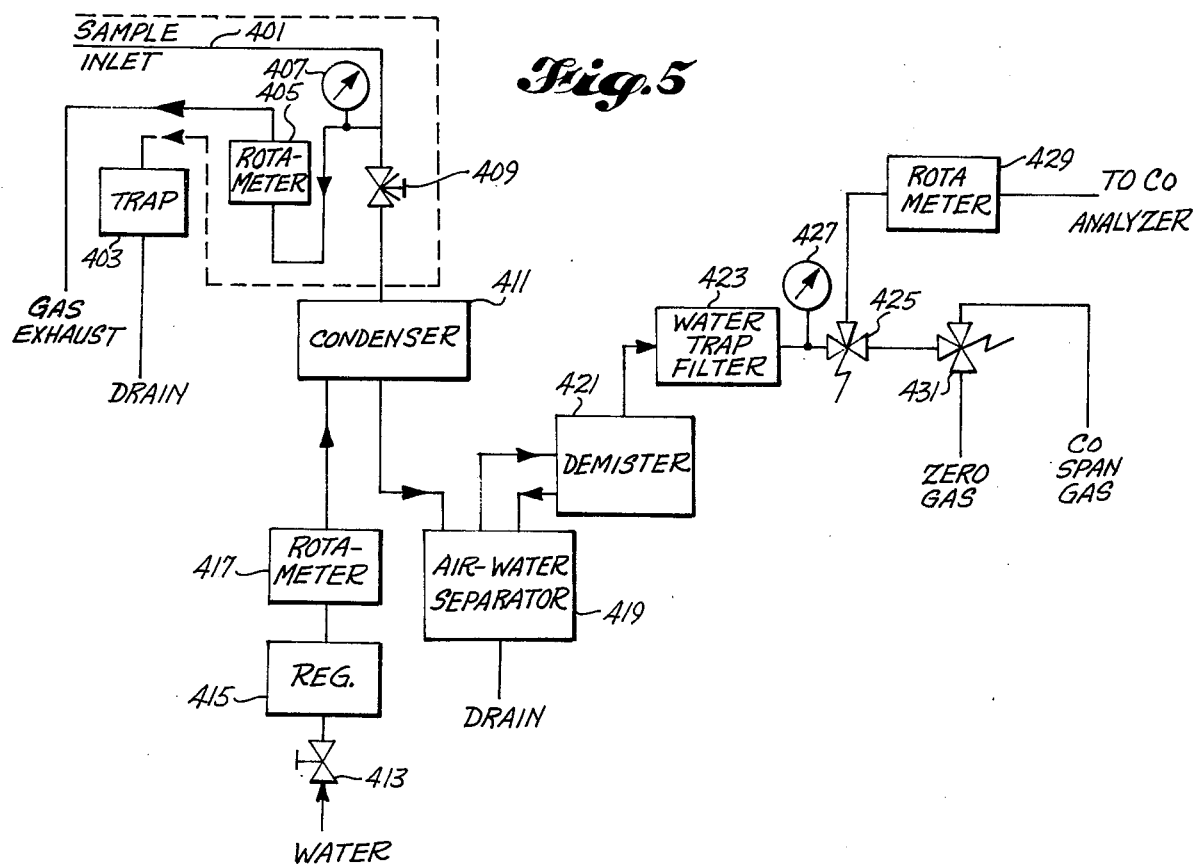

FIG. 5 is a partially block and partially schematic diagram of a CO conditioner and regulator suitable for use in the embodiment of the invention illustrated in FIG. 1 to connect the second sample conditioner 21 to the second CO analyzer 73. The CO conditioner and regulator illustrated in FIG. 5 includes a sample inlet 401. The steam conduit of the heater pipe 32 running to the sample inlet 401 is connected to a drain via a trap 403. The sample inlet 401 is connected to a gas exhaust via a gas rotameter 405, which may be a 0–40 l/M rotameter. A pressure gauge 407 is also connected to the sample inlet to provide a measure of sample pressure.

The sample inlet 401 is further connected via a mechanically actuated regulating valve 409 to the inlet of a condensor 411. Water from a suitable source is connected via a mechanically controlled valve 413 in series with a regulator 415 and a water rotameter 417 to the water inlet of the condensor 411. The water rotameter may be a 0–40 GPH rotameter, for example. The outlet of the condensor 411 is connected to the inlet of an air-water separator 419. The water outlet of the air-water separator is connected to a drain. The gas outlet of the air-water separator 419 is connected to the inlet of a demister 421. The water outlet of the demister 421 is recirculated back to the air-water separator 419.

The gas outlet of the demister 421 is connected to the inlet of a water trap filter 423. The outlet of the water trap filter 423 is connected to one inlet of a first electrically controlled three-way valve 425. In addition, the outlet of the water trap filter is connected to a pressure gauge 427. The outlet of the first electrically controlled three-way valve 425 is connected to the inlet of a CO rotameter 429. The outlet of the CO rotameter 429 is connected to the inlet of the second CO analyzer 73. The CO rotameter may be a 0–12 SCFH rotameter, for example.

The second inlet of the first electrically controlled three-way valve 425 is connected to the outlet of a second electrically controlled three-way valve 431. The first inlet of the second electrically controlled three-way valve 431 is connected to a zero gas source and the second inlet is connected to a CO span gas source.

As with the CO conditioner and regulator illustrated in FIG. 4, the CO conditioner and regulator illustrated in FIG. 5 conditions the sample gas such that it becomes suitable for application to a CO analyzer, in this case, the analyzer may be, preferably, a Beckman 864 CO analyzer, referenced above. In addition, the CO conditioner and regulator provides for the application of zero gas and CO span gas to the CO analyzer for calibration purposes.

It will be appreciated from the foregoing description that the invention comprises a method of and an apparatus for monitoring an atmosphere and indicating when predetermined percents of the LEL of the atmosphere exist, either with respect to the amount of combustible organic vapors or with respect to the amount of the carbon monoxide, or both. When the predetermined percents are reached, related alarms are energized. The invention may be designed such that alarms are energized as increasingly higher levels of either combustible organic vapors or carbon monoxide, or a combination of both, are found to exist in the atmosphere being monitored. The invention is redundant in that it provides for analysis of the gases obtained from two different regions of the atmosphere. If desired, additional gas regions could be sampled and analyzed.

While a preferred embodiment of the invention has been illustrated and described, it will be appreciated that various changes can be made herein without departing from the spirit and scope of the invention. For example, the denoted 15 and 30 percent LEL based on combustible organic vapors or CO content and the 40 and 60 percent LEL based on combined content figures used to control their related alarms are conservative arbitrary figures. Thus, these figures can be raised or lowered as depending upon factors making up a specific environment of use of the invention. Also, the $O_2$, CO, combustible organic vapors and total recorders, illustrated as separate recorders, could be replaced by a single, multitrack recorder. Hence, the invention can be practiced otherwise than as specifically described herein.

The embodiments of the invention in which an exclusive property or privilege is claimed are defined as follows:

1. A method of monitoring an atmosphere containing combustibles to provide an indication of the inflammability potential of the atmosphere in terms of LEL based on the level of combustibles in the atmosphere being monitored, said method comprising the steps of:
  sampling the atmosphere to obtain samples thereof;
  determining the combustible organic vapors content of the samples in terms of percent LEL based on the total carbon atom concentration of combustible organic vapors present in the samples;
  determining if the combustible organic vapors content of the samples is above a predetermined percent LEL;
  providing an indication when the combustible organic vapors content is above said predetermined percent LEL;
  determining the carbon monoxide content of the samples in terms of percent LEL based on carbon monoxide present in the samples;
  determining if the carbon monoxide content of the samples is above a predetermined percent LEL; and
  providing an indication when the carbon monoxide content is above said predetermined percent LEL.

2. The method claimed in claim 1 including the step of removing undesirable constituents from said samples prior to said steps of: determining the combustible organic vapors content of the samples in terms of percent LEL based on the total carbon atom concentration of combustible organic vapors present in the samples; and, determining the carbon monoxide content of the samples in terms of percent LEL based on carbon monoxide present in the samples.

3. A method of monitoring an atmosphere containing combustibles to provide an indication of the inflammability potential of the atmosphere in terms of LEL based on the level of combustibles in the atmosphere being monitored, said method comprising the steps of:
  sampling the atmosphere at at least two different points;
  determining the combustible organic vapors content of the samples in terms of percent LEL based on the total carbon atom concentration of combustible organic vapors present in the samples;
  determining whether or not the combustible organic vapors content of any of the samples is above a predetermined percent LEL;
  providing an indication when the combustible organic vapors content of any of the samples is above said predetermined percent LEL;
  determining the carbon monoxide content of the samples in terms of percent LEL based on the carbon monoxide present in the samples;
  determining whether or not the carbon monoxide content of any of the samples is above a predetermined percent LEL; and,
  providing an indication when the carbon monoxide content of any of the samples is above said predetermined percent LEL.

4. The method claimed in claim 3 includes the step of removing undesirable constituents from said samples prior to the steps of: determining the combustible organic vapors content of the samples in terms of percent LEL based on the total carbon atom concentration of combustible organic vapors present in the samples; and, determining the carbon monoxide content of the samples in terms of percent LEL based on the carbon monoxide present in the samples.

5. The method claimed in claim 4 including the further steps of:
  comparing the combustible organic vapors content of the samples, determined in terms of percent LEL based on the total carbon atom concentration of combustible organic vapors present in the samples to select which of the samples has the highest combustible organic vapors content;
  comparing the determined percent LEL based on the carbon monoxide content of the samples to select which of the samples has the highest carbon monoxide content; and,
  recording the combustible organic vapors content and carbon monoxide content selected by said comparisons.

6. The method claimed in claim 5 including the further steps of:
  comparing the combustible organic vapors content of the samples, determined in terms of percent LEL based on the total carbon atom concentration of combustible organic vapors present in the samples, to determine if the difference therebetween is above a predetermined differential combustible organic vapors level;
  providing an indication when said comparison determines that said difference is above said predetermined differential combustible organic vapors level;
  comparing the determined percent LEL based on the carbon monoxide content of the samples to determine if the difference therebetween is above a predetermined differential carbon monoxide level; and,
  providing an indication when said comparison determines that said difference is above said predetermined differential carbon monoxide level.

7. A method of monitoring an atmosphere containing combustibles to provide an indication of the inflammability potential of the atmosphere in terms of LEL based on the level of combustibles in the atmosphere being monitored, said method comprising the steps of:
  sampling the atmosphere to obtain samples thereof;
  determining the combustible organic vapors content of the samples in terms of percent LEL based on the total carbon atom concentration of combustible organic vapors present in the samples;
  determining the carbon monoxide content of the samples in terms of percent LEL based on carbon monoxide present in the samples;
  combining the combustible organic vapors content in terms of percent LEL with the carbon monoxide content in terms of percent LEL to derive a total combustibles content in terms of percent LEL; and,
  providing an indication of the total combustibles content of said samples.

8. The method claimed in claim 7 including the step of removing undesirable constituents from said samples prior to said steps of: determining the combustible organic vapors content of the samples in terms of percent LEL based on the total carbon atom concentration of combustible organic vapors present in the samples; and, determining the carbon monoxide content of the samples in terms of percent LEL based on carbon monoxide present in the samples.

9. The method claimed in claim 7 including the further steps of:
  determining if the total combustibles content of the samples is above a predetermined percent LEL; and, providing an indication when the total combustibles content is above said predetermined percent LEL.

10. A method of monitoring an atmosphere containing combustibles to provide an indication of the inflammability potential of the atmosphere in terms of LEL based on the level of combustibles in the atmosphere being monitored, said method comprising the steps of:
sampling the atmosphere at at least two different points;
determining the combustible organic vapors content of the samples in terms of percent LEL based on the total carbon atom concentration of combustible organic vapors present in the samples;
determining the carbon monoxide content of the samples in terms of percent LEL based on the carbon monoxide present in the samples;
combining the combustible organic vapors content in terms of percent LEL with the carbon monoxide content in terms of percent LEL to derive a total combustibles content in terms of percent LEL; and,
providing an indication of the total combustibles content of the samples.

11. The method claimed in claim 10 including the step of removing undesirable constituents from said samples prior to the steps of: determining the combustible organic vapors content of the samples in terms of percent LEL based on the total carbon atom concentration of combustible organic vapors present in the samples; and, determining the carbon monoxide content of the samples in terms of percent LEL based on the carbon monoxide present in the samples.

12. The method claimed in claim 10 including the further steps of:
determining if the total combustibles content of any of the samples is above a predetermined percent LEL; and,
providing an indication when the total combustibles content of any of the samples is above said predetermined percent LEL.

13. The method claimed in claim 10 including the further steps of:
comparing the combustible organic vapors content of the samples, determined in terms of percent LEL based on the total carbon atom concentration of combustible organic vapors present in the samples, to select which of the samples has the highest combustible organic vapors content;
comparing the determined percent LEL based on the carbon monoxide content of the samples to select which of the samples has the highest carbon monoxide content; and,
combining the combustible organic vapors content and carbon monoxide content selected by said comparison to obtain said total combustibles content.

14. The method clamed in claim 13 including the further steps of:
comparing the combustible organic vapors content of the samples, determined in terms of percent LEL based on the total carbon atom concentration of combustible organic vapors present in the samples, to determine if the difference therebetween is above a predetermined differential combustible organic vapors level;
providng an indication when said comparison determines that said difference is above said predetermined differential combustible organic vapors level;
comparing the determined percent LEL based on the carbon monoxide content of the samples to determine if the difference therebetween is above a predetermined differential carbon monoxide level; and,
providing an indication when said comparison determines that said difference is above said predetermined differential carbon monoxide level.

15. Apparatus for monitoring a potentially inflammable atmosphere containing combustibles to provide an indication of the inflammability of the atmosphere in terms of LEL based on the level of combustibles in the atmosphere, said apparatus comprising:
sampling means for sampling said atmosphere to obtain samples of said atmosphere;
combustible organic vapors analyzing means connected to said sampling means for determining the combustible organic vapors content of said samples in terms of LEL based on the total carbon atom concentraction of combustible organic vapors present in the samples;
combustible organic vapors indicating means connected to said combustible organic vapors analyzing means for providing an indication when said percent LEL based on the total carbon atom concentration of combustible organic vapors present in the samples;
carbon monoxide content analyzing means connected to said sampling means for determining the carbon monoxide content of said samples in terms of percent LEL based on the carbon monoxide present in the samples; and, and,
carbon monoxide indicating means connected to said carbon monoxide content analyzing means for providing an indication when said percent LEL based on the carbon monoxide present in the samples is above a predetermined percent LEL.

16. The apparatus claimed in claim 15 wherein said combustible organic vapors analyzing means is a flame ionization detecting means.

17. The apparatus claimed in claim 16 wherein:
said sampling means includes at least two samplers for obtaining spaced independent samples of said atmosphere;
said flame ionization detecting means includes at least two flame ionization detectors, one connected to each of said samplers for receiving samples therefrom and determining the combustible organic vapors content of said samples in terms of LEL based on the total carbon atom concentration of combustible organic vapors present in the samples; and,
said combustible organic vapors analyzing means includes combustible organic vapors high selector means connected to said flame ionization detectors for selecting the highest output of said flame ionization detectors and applying said selected output to said combustible organic vapors indication means.

18. The apparatus claimed in claim 17 wherein said carbon monoxide content analyzing means includes:
at least two carbon monoxide analyzers, one connected to each to said samplers for receiving samples therefrom and determining the combustible carbon monoxide content of said samples in terms of LEL based on the carbon monoxide present in the samples; and, a carbon monoxide high selector connected to the outputs of said carbon monoxide analyzer for selecting the highest output of said carbon monoxide analyzers and applying said selected output to said carbon monoxide indicating means.

19. The apparatus claimed in claim 18 wherein:
said combustible organic vapors indicating means includes first and second alarms, said first alarm being activated when the output of said combustible organic vapors high selector achieves a first level and said second alarm being activated when the output of said combustible organic vapors high selector achieves a second level, said second level being higher than said first level; and,
said carbon monoxide indicating means includes first and second alarms, said first alarm being activated when the output of said carbon monoxide high selector achieves a first level and said second alarm being activated when the output of said carbon monoxide high selector achieves a second level, said second level being higher than said first level.

20. The apparatus claimed in claim 19 including first and second sample conditioners, said first sample conditioner connected between the output of said first sampler and the inputs of one of said flame ionization detectors and one of said carbon monoxide analyzer and said second sample conditioner connected between the output of said second sampler and the inputs of the other of said flame ionization detectors and the other of said carbon monoxide analyzers.

21. The apparatus claimed in claim 20 including a combustible organic vapors differential switch connected to the outputs of said first and second flame ionization detectors and a combustible organic vapors differential pressure alarm connected to the output of said differential pressure switch such that said pressure alarm is activated when the difference between the outputs of said first and second flame ionization detectors reaches a predetermined differential level.

22. The apparatus claimed in claim 21 including a carbon monoxide differential pressure switch connected to the output of said first and second carbon monoxide analyzers and a carbon monoxide differential pressure alarm connected to the output of said differential pressure switch such that said differential pressure alarm is activated when the difference between the outputs of said carbon monoxide analyzers reaches a predetermined differential level.

23. The apparatus claimed in claim 22 including an oxygen analyzer connected to one of said samplers for determining the oxygen content thereof; and, a recording means connected to the outputs of said combustible organic vapors high selector, said carbon monoxide high selector and said oxygen analyzer for recording the outputs of said combustible organic vapors high selector, said carbon monoxide high selector and said oxygen analyzer.

24. Apparatus for monitoring a potentially inflammable atmosphere containing combustibles to provide an indication of the inflammability of the atmosphere in terms of LEL based on the level of combustibles in the atmosphere, said apparatus comprising:
sampling means for sampling said atmosphere to obtain samples of said atmosphere;
combustible organic vapors analyzing means connected to said sampling means for determining the combustible organic vapors content of said samples in terms of LEL based on the total carbon atom concentration of combustible organic vapors present in the samples;
carbon monoxide content analyzing means connected to said sampling means for determining the carbon monoxide content of said samples in terms of percent LEL based on the carbon monoxide present in the samples;
combining means connected to said combustible organic vapors analyzing means and said carbon monoxide content analyzing means for combining said combustible organic vapors content with said carbon monoxide content to provide a total combustibles content in terms of percent LEL based on the total carbon atom concentration of combustible organic vapors and the carbon monoxide present in the samples; and,
total combustibles indicating means connected to said combining means for providing an indication of the total combustible content of said samples.

25. The apparatus claimed in claim 24 wherein said total combustibles indicating means includes an alarm that provides an indication when said total combustibles content is above a predetermined level.

26. The apparatus claimed in claim 24 wherein said combustible organic vapors analyzing means is a flame ionization detecting means.

27. The apparatus claimed in claim 26 wherein:
said sampling means includes at least two samplers for obtaining spaced independent samples of said atmosphere;
said flame ionization detecting means includes at least two flame ionization detectors, one connected to each of said samplers for receiving samples therefrom and determining the combustible organic vapors content of said samples in terms of LEL based on the total carbon atom concentration of combustible organic vapors present in the samples; and,
said combustible organic vapors analyzing means includes combustible organic vapors high selector means connected to said flame ionization detectors for selecting the highest output of same flame ionization detectors and applying said selected output to said combining means.

28. The apparatus claimed in claim 27 wherein said carbon monoxide content analyzing means includes:
at least two carbon monoxide analyzers, one connected to each of said samplers for receiving samples therefrom and determining the combustible carbon monoxide content of said samples in terms of LEL based on the carbon monoxide present in the samples; and,
a carbon monoxide high selector connected to the outputs of said carbon monoxide analyzers for selecting the highest output of said carbon monoxide analyzers and applying said selected output to said combining means.

29. The apparatus claimed in claim 28 wherein:
said total combustibles indicating means includes first and second alarms, said first alarm being activated when the output of said combining means achieves a first level and said second alarm being activated when the output of said combining means achieves a second level, said second level being higher than said first level.

30. The apparatus claimed in claim 29 including first and second sample conditioners, said first sample conditioner connected between the output of said first sampler and the inputs of one of said flame ionization detectors and one of said carbon monoxide analyzers and said second sample conditioner connected between the output of said second sampler and the inputs of the other of said flame ionization detectors and the other of said carbon monoxide analyzers.

31. The apparatus claimed in claim 30 including a controller connected to the output of said combining means and a vent means associated with said atmosphere and connected to said controller such that said vent means is controlled in accordance with the output of said combining means.

32. The apparatus claimed in claim 31 including an oxygen analyzer connected to one of said samplers for determining the oxygen content thereof; and, a recording means connected to the outputs of said combining means and said oxygen analyzer for recording the outputs of said combining means and said oxygen analyzer.

* * * * *

UNITED STATES PATENT AND TRADEMARK OFFICE
CERTIFICATE OF CORRECTION

PATENT NO. : 4,069,018
DATED : January 17, 1978
INVENTOR(S) : Karna et al

It is certified that error appears in the above-identified patent and that said Letters Patent are hereby corrected as shown below:

Columns 5 and 6, in the Compound table, in the last row (LEL x N), in the third line down, delete "6.03" and insert —6.05—.

Column 8, line 34, delete "occuring" and insert —occurring—.
Column 8, line 40, delete "analzyer" and insert —analyzer—.
Column 8, line 46, delete "ther" and insert —the—.
Column 9, line 31, delete "containuous" and insert —continuous—.
Column 9, line 52, delete "fo" and insert —of—.
Column 17 (Claim 14) line 67, delete "providng" and insert —providing—.
Column 18 (Claim 15) line 22, delete "concentraction" and insert —concentration—.
Column 18 (Claim 15) line 34, delete the second occurrence of "and,".

Signed and Sealed this

Sixteenth Day of May 1978

[SEAL]

Attest:

RUTH C. MASON
Attesting Officer

LUTRELLE F. PARKER
Acting Commissioner of Patents and Trademarks